United States Patent
Desecki et al.

[11] Patent Number: 5,964,785
[45] Date of Patent: Oct. 12, 1999

[54] BAYONET LOOK CANNULA FOR PRE-SLIT Y-SITE

[75] Inventors: Vincent C. Desecki, Ingleside; Thomas E. Dudar, Palatine; Michael J. Finley, Park City, all of Ill.

[73] Assignee: Baxter International Inc., Deerfield, Ill.

[21] Appl. No.: 08/486,119

[22] Filed: Jun. 7, 1995

Related U.S. Application Data

[62] Division of application No. 08/021,644, Feb. 22, 1993, which is a continuation of application No. 07/435,638, Nov. 9, 1989, abandoned, which is a continuation-in-part of application No. 07/217,004, Jul. 8, 1988, abandoned, which is a continuation-in-part of application No. 07/147,414, Jan. 25, 1988, abandoned.

[51] Int. Cl.$^6$ .................................................. A61M 29/00
[52] U.S. Cl. ............................................................. 606/280
[58] Field of Search ...................................... 604/167, 169, 604/174, 239–243, 271–274, 283, 412–416, 905

[56] References Cited

U.S. PATENT DOCUMENTS 4,745,950  5/1988  Mathieu .
4,810,241  3/1989  Rogers .

FOREIGN PATENT DOCUMENTS

6842519  10/1985  Germany .

*Primary Examiner*—William Lewis
*Attorney, Agent, or Firm*—Jeffrey C. Nichols; Mark J. Buonaiuto; Francis C. Kowalik

[57] ABSTRACT

A cannula and injection site coupling system comprising a cannula or piercing member assembly having a blunt cannula partially surrounded by a protective shield. The protective shield is spaced apart from the blunt cannula and includes a bayonet arm, a bayonet barb, a bayonet lock and an opening or gap. The injection site has a septum with a opening and an arm. When the cannula assembly and injection site are coupled, the injection site arm is lodged within the cannula assembly lock opening.

5 Claims, 10 Drawing Sheets

BAYONET LOOK CANNULA FOR PRE-SLIT Y-SITE

CROSS-REFERENCE TO RELATED APPLICATION

This is a division of application Ser. No. 08/021,644, filed Feb. 22, 1993 which is a continuation of application of Ser. No. 07/435,638, filed on Nov. 9, 1989, now abandoned, which is a continuation-in-part application of the commonly assigned U.S. patent application, Ser. No. 217,004 entitled "Pre-Slit Injection Site and Tapered Cannula" filed Jul. 8, 1988, now abandoned, which is a continuation-in-part application of the commonly assigned U.S. patent application, Ser. No. 147,414 entitled "Pre-Slit Injection Site And Associated Cannula" filed Jan. 25, 1988, now abandoned. Both patent applications are herein incorporated by reference and made part of this patent application as though they were reproduced completely herein.

FIELD OF THE INVENTION

The invention pertains to coupling systems usable to transfer materials from one flow conduit to another. More particularly, the invention pertains to two-part coupling members with a first part including a pre-slit septum and a second part including a blunt cannula at least partially surrounded by a protective shield. The pre-slit septum slidably receives the blunt cannula to effect the coupling. The systems have particular applicability in the medical field for handling medications and body fluids.

BACKGROUND OF THE INVENTION

In the medical field, injection sites usable with pointed cannulae have long been known. For example, such sites can be formed with a housing having a fluid flow path therein. A septum is positioned in the housing closing the fluid flow path.

One injection site usable with a piercing cannula is disclosed in U.S. Pat. No. 4,412,573 to Zdeb entitled "Injection Site." The Zdeb patent is assigned to Assignee of the present invention.

The pointed cannula can be forced through the septum into fluid flow communication with the flow path in the housing. Known injection sites usable with a piercing cannula can be physically damaged by repetitive piercing caused by the sharp cannula. This damage, known as coring or laceration, can result in subsequent leakage.

Due to problems associated with infectious agents, personnel using such pointed cannulae do so with great care. Notwithstanding careful and prudent practice, from time to time, accidents do occur and individuals using such pointed cannulae jab themselves.

Injection sites usable with a blunt cannula are also known. For example, U.S. Pat. No. 4,197,848 issued to Garrett et al. entitled "Closed Urinary Irrigation Site" and assigned to the Assignee of the present invention discloses one such injection site. That injection site is a relatively low pressure device having a relatively thin, molded, sealing member. The sealing member has an opening therethrough.

A blunt cannula can be forced through the sealing member placing the cannula into fluid flow communication-with a fluid flow pathway in the injection site.

Injection sites of the type noted above usable with a blunt cannula have the advantage that the blunt cannula will not pierce the skin of a user. On the other hand, it is important that the pre-slit injection site reseal with enough force that fluids do not ooze therefrom and that airborne particulate matter, bacterial or viral matter do not enter therethrough.

Hence, there continues to be a need for a pre-slit injection site which can be used with a variety of solutions and over a range of fluid pressures. Further, there continues to be a need for such a pre-slit injection site which will reliably reseal even after many insertions of the blunt cannula.

Such an injection site should be able to receive a large number of insertions of the cannula without displaying reseal failure and without allowing the cannula to drop out of contact. Such an injection site should provide for improved alignment of the cannula on insertion. Improved alignment will result in less chance of damage to the injection site after repeated insertions of the cannula. Preferably, the injection site would also be usable with a pointed cannula. Preferably, a pre-slit injection site usable with a blunt cannula will provide a reasonable level of insertion force such that health care personnel will readily be able to insert the blunt cannula, yet the cannula will not easily fall from or drop out of contact with the septum.

SUMMARY OF THE INVENTION

In accordance with the invention, an easily wipeable Y-type injection site or Y-site usable with a bayonet lock cannula is provided.

The bayonet lock cannula includes a blunt cannula which may be of several designs surrounded by a protective shield. The protective shield includes an arcuate wall with a bayonet arm and barb to provide a bayonet lock. As the bayonet lock cannula is inserted onto the Y-site, the Y-site arm passes through the gap between the bayonet arm and the arcuate wall. Both the bayonet lock cannula and the Y-site have dimensions to create four zones of interference. These zones of interference properly align the Y-site and bayonet lock cannula with respect to one another so that the piercing member will be perpendicular to the Y-site septum or sealing member.

The injection site includes a housing which defines a fluid flow channel therethrough. The housing has a first and a second end.

A flexible sealing member is carried by the housing for sealing the first end. The sealing member has a resealable opening therein. The sealing member also is formed with a curved exterior peripheral surface such that the blunt cannula can be sealingly inserted through the opening and placed in fluid flow communication with the flow path. Further, the blunt cannula can be removed from the opening with the sealing member then interacting with the housing so as to reseal the opening.

The housing can also be formed with the first end including an annular channel underlying the sealing member. The sealing member is subjected to radially directed forces by a tapered surface of the first end of the housing. These forces tend to reseal the opening in the sealing member.

The sealing member can be a cylindrically shaped rubber member. The first end of the housing can include an interior tapered surface for receiving the sealing member and for applying the radially directed forces to the sealing member.

A retaining member carried by the first end of the housing can be used to retain the sealing member with the housing. The retaining member can be generally U-shaped. Alternately, the retaining member can be formed as a coiled spring.

The retaining member applies axially directed forces to the sealing member. In one embodiment of the invention, the retaining member deflects the sealing member and forms a cured exterior peripheral surface thereon. The curved exterior peripheral surface is an easily wipeable surface.

The retaining member deflects or distorts the upper and lower peripheral edges slightly as a result of applying axial forces thereto. When the blunt piercing member is inserted into the slit in the sealing member, an annular interior peripheral region of the sealing member deforms further and fills, at least in part, the annular channel.

Deformation of this annular peripheral region results in an insertion force in a range of 2.0 to 5 pounds. Preferably, the insertion force will have a value of the order of 2.0 pounds.

The resealable opening in the sealing member can extend entirely through that member. Alternately, the resealable opening can extend only partway therethrough. In this embodiment, the end of the blunt cannula will be used to tear through the remainder of the sealing member.

The sealing member can be formed in two parts. An exterior cylindrical portion can be slit completely. An interior cylindrical unslit portion can be provided to seal the site until the blunt cannula is inserted therethrough the first time.

The interior surface of the first end can be formed with the taper in a range on the order of 5 degrees to 20 degrees. Preferably, the interior surface will have a taper on the order of 12 degrees. This tapered surface permits the use of a cylindrically shaped sealing member.

To provide for leak-free insertion, the length of the slit in the sealing member must be less than one-half of the circumference of the cannula being inserted therethrough. Hence, the slit length may exceed the diameter of the cannula being inserted. In addition, the slit length must be great enough, given the elastic limit of the sealing member, to prevent tearing during insertion.

Further in accordance with the invention, a coupling system for coupling first and second fluid flow members together is provided. The coupling system includes an injection site which is affixed to the first fluid flow member. The injection site includes a housing. The housing has a fluid flow path therethrough.

A sealing member is carried by the housing. The sealing member has a resealable opening therein.

An annular retaining member is carried by the housing and cooperates with the housing to retain the sealing member therein. Radially directed forces are applied to the sealing member by the housing, thereby urging the opening into a resealed condition.

A blunt cannula, affixed to a second fluid flow member, has a fluid flow path therethrough. The cannula engages the housing when the cannula extends through the opening of the sealing member. When so positioned, the two fluid flow members are placed into fluid flow communication.

Numerous other advantages and features of the present invention will become readily apparent from the following detailed description of the invention and the embodiments thereof, from the claims and from the accompanying drawings in which the details of the invention are fully and completely disclosed as a part of this specification.

DETAILED DESCRIPTION OF A PREFERRED EMBODIMENT

While this invention is susceptible of embodiment in many different forms, there are shown in the drawings and will be described herein in detail specific embodiments thereof with the understanding that the present disclosure is to be considered as an exemplification of the principles of the invention and is not intended to limit the invention to the specific embodiments illustrated.

Figure 1:
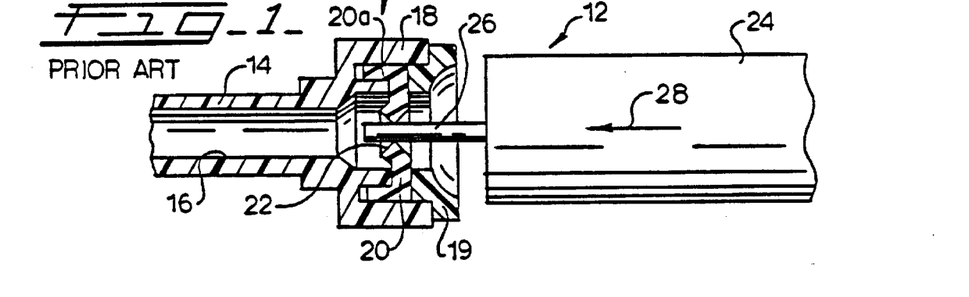
FIG. 1 is a side elevational view, partly in section, of a prior art pre-slit injection site and an associated blunt cannula.

A prior art pre-slit injection site 10 and associated blunt cannula 12 are illustrated in FIG. 1. The prior art injection site 10 has a cylindrical housing 14 with a fluid flow path 16 therethrough. A first end 18 of the housing 14 is closed with a relatively thin disc-shaped resealable member 20. The member 20 has a resealable opening 22 therein.

The member 20 is a molded septum with an integrally formed skirt 20a. The skirt 20a is oriented generally perpendicular to the portion of the septum with the opening 22.

The cannula 12 includes a body portion-24 which carries at a first end a hollow, cylindrical, blunt piercing member 26. As the cannula 12 is moved in a direction 28 toward the first end 18 of the injection site 10, the member 26 slidably engages the opening 22. The sealing member 20 is then deformed adjacent the opening 22 and the member 26 extends into the flow path 16. A fluid flow path through the cannula 12 will then be in fluid flow communication with the flow path 16 via the hollow piercing member 26.

Figure 2:
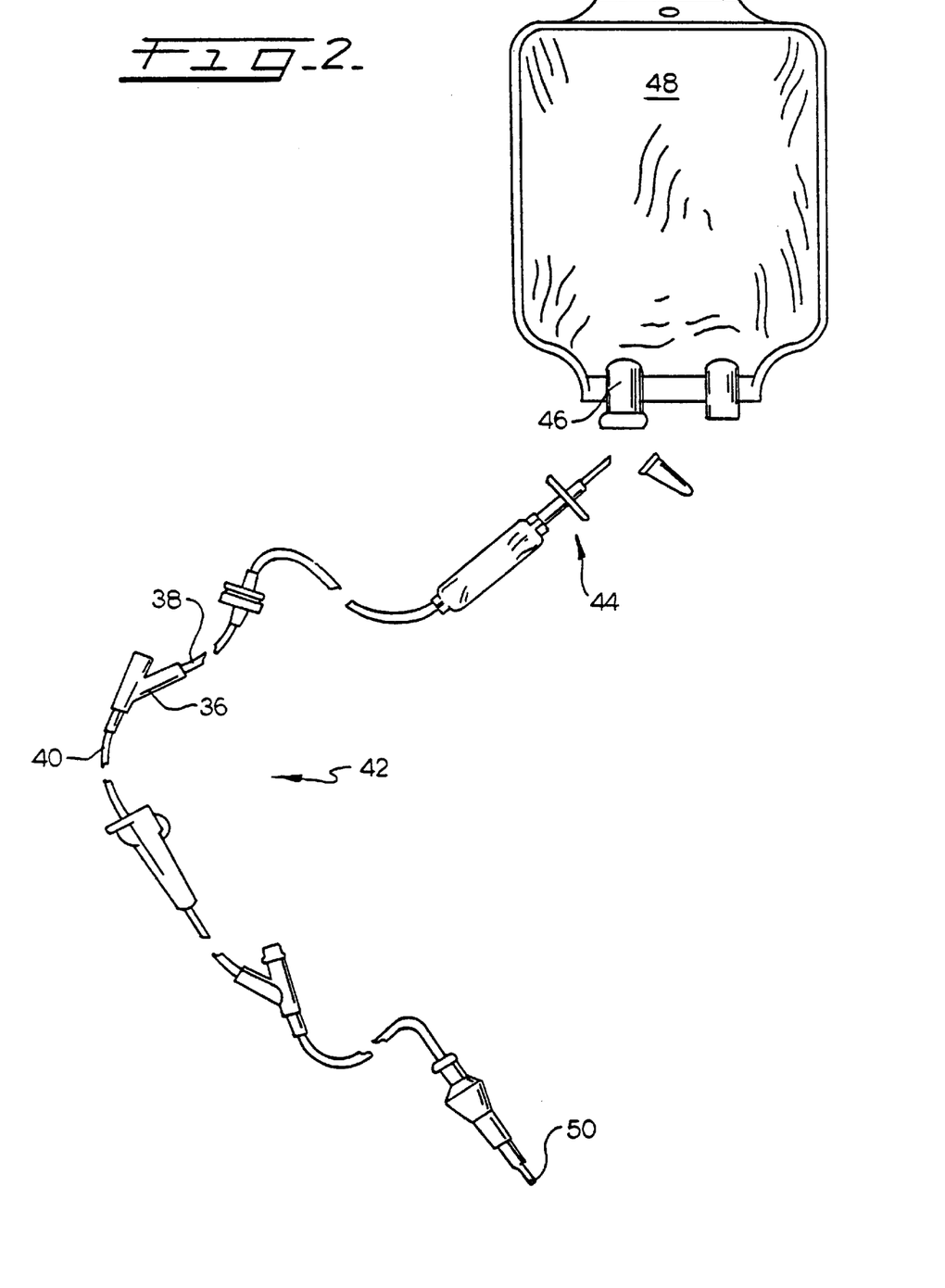
FIG. 2 is an overall view of a container, an associated solution administration set and a pre-slit injection Y-site in accordance with the present invention.
Figures 3, 4:
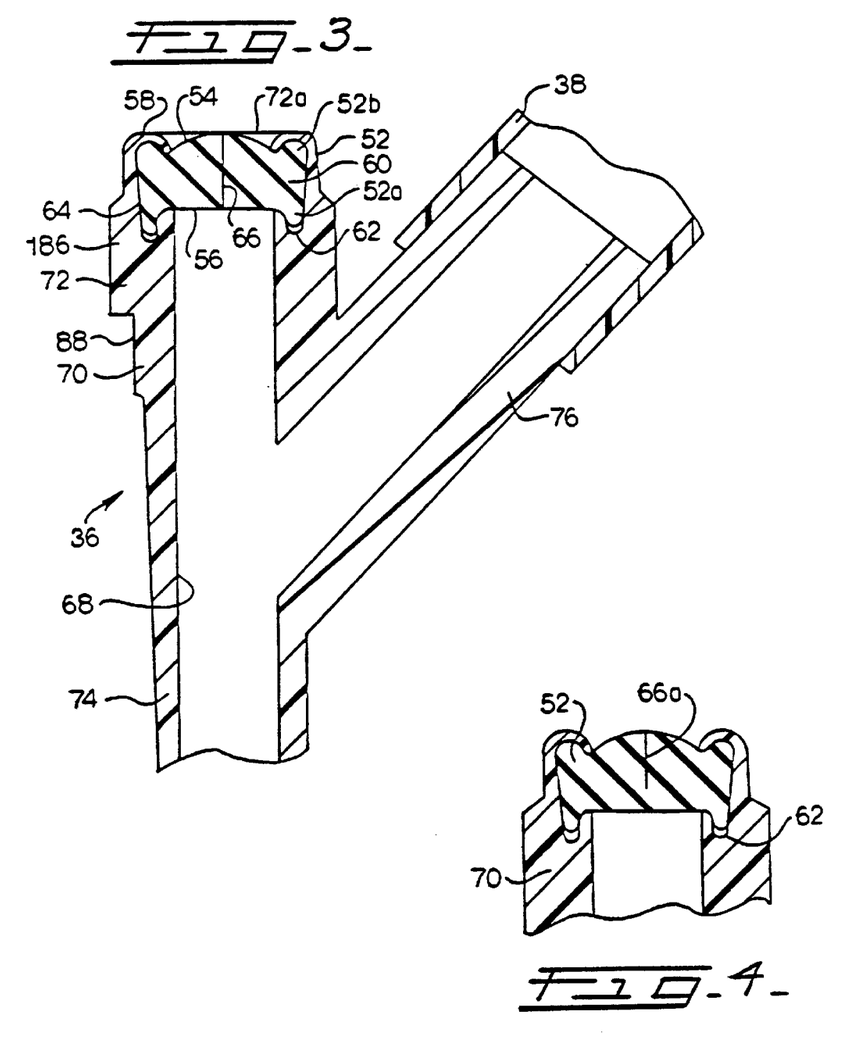
FIG. 3 is a side view of the Y-site connector in section carrying a pre-slit injection site in accordance with the present invention.
FIG. 4 is an enlarged fragmentary side view in section of a coupling member carrying a pre-slit injection site where the slit extends only partway through the septum.

FIGS. 2 and 3 illustrates a pre-slit septum 52 in a Y-site connector or Y-site 36 which is connected to first and second pieces of tubing, 38 and 40, respectively. FIG. 2 shows a fluid administration set 42 of a conventional variety except that it includes as a component the pre-slit Y-site 36. The set 42 includes a spike connection 44 at a first end designed to pierce the port 46 of the container 48. The set 42 may also include other components such as adjustable clamps or filters. At the second end of the set 42 is a piercing member 50 which connects the fluid flow to the patient, such as through a vein in the hand of the patient.

As shown in FIG. 3, Y-site 36 is formed with a cylindrical housing 70 having a first end 72, and a second end 74 and one arm 76. As discussed above, the second end 74 is bounded to second tubing 40 and the arm 76 is bounded to first tubing 38. The primary flow of fluid is from container 48 through arm 76 and second end 74 to the patient. The secondary fluid flow from a second container, syringe or other medical device (not shown) is through first end 72 and second end 74 to the patient. The primary fluid and the secondary fluid are mixed in the second end 74 of the Y-site housing and in second tubing 40.

FIG. 3 illustrates, in section, further details of the Y-site 36. A resealable septum 52 is carried by the first end 72 of the housing 70. The septum 52 includes first and second spaced apart surfaces 54 and 56 respectively. The surface 54 has been forced into a dome-like shape by annular, U-shaped, swaged end members 58 carried by the first end 72. The dome-like shape of the surface 54 can extend beyond a surface 72a of the first end 72. This facilitates cleaning the surface 54.

The septum 52 has a generally cylindrical shape. The septum 52 can be formed of a latex or synthetic rubber material. Alternately, the septum can be formed of a thermoplastic elastomer. The material used for the septum 52 should be non-toxic and sterilizable such as by means of radiation, steam or ethylene oxide.

Because the septum 52 is generally cylindrical in shape, it can be die-cut from a sheet, cut from an extruded rod or molded. The septum 52 can have an exemplary diameter on the order of 0.30 inches. The height of the septum 52 can be, for example, on the order of 0.125 inches.

The first end 72 is also formed with a tapered interior surface 60 which terminates in an annular channel 62. The tapered interior surface 60 has a taper in a range of 5 degrees to 20 degrees. Preferably, the taper will be on the order of 7 degrees. With the indicated size of the above noted exemplary septum 52 and a 7 degree taper, diametric resealing compression of the septum 52 adjacent the channel 62 is on the order of 10%.

The channel 62 is bounded in part by a septum supporting ridge 62a. The channel 62 can typically have a depth in a range of 0.050–0.070 inches.

A peripheral surface 64 of the septum 52 slidably engages the tapered interior surface 60 as the septum 52 slides into the first end 72. The annular channel 62 which underlies the interior peripheral surface 64 of the septum 52 is provided to permit the septum 52 to deform when a blunt cannula is inserted through an opening 66 therein.

The swaged end members 58 apply axial forces to the septum 52 thereby creating the domed exterior peripheral surface 54. The axial forces applied by the end members 58 slightly deform the regions 52a and 52b. The tapered internal surface 60 applies radially directed forces to the septum 52, thereby forcing the opening 66 into a resealed condition.

In an alternate embodiment, the surface 54 could be formed as a flat, as opposed to a domed, surface.

Once the Y-site 36 is lockingly engaged with the bayonet lock cannula 82, as will be discussed later, a sealed system is formed through which fluids can be infused into the Y-site 36. The resealable septum 52 closes the fluid flow path through Y-site 36 when the bayonet lock cannula 82 is disengaged.

As discussed in the copending patent applications incorporated by reference, the injection site and blunt cannula may be adapted for use with a variety of medical instruments, including, but not limited to a syringe with luer locking connection, a blunt cannula with deflecting lever locking members, or a spike connection for an IV solution bag.

Figure 5:
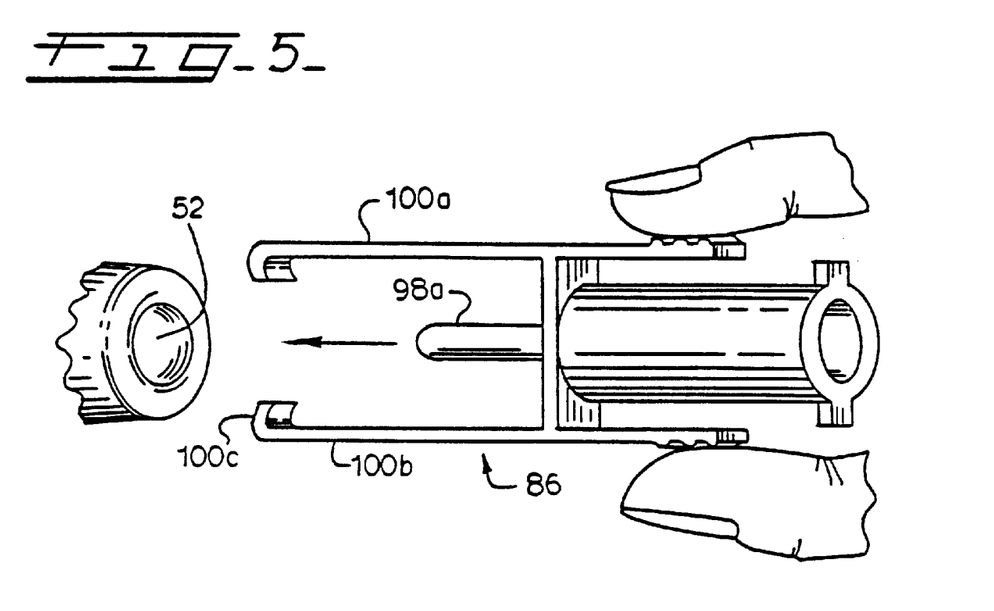
FIG. 5 is a perspective view of a blunt cannula with lever locking members prior to engaging the pre-slit septum of an injection site.

In addition to being used with the bayonet locking cannula 82 of FIGS. 7–13, the Y-site of the present invention may be also used with a variety of other cannulas, including the blunt cannula 86 of FIG. 5 or the cannulas shown in FIGS. 14 through 18.

FIG. 5 illustrates the pre-slit injection Y-site used with a blunt cannula 86 to two spring-like deflecting lever arms 100a and 100b. The curved end regions 100c of the lever members 100a and 100b slidingly engage the offset surface 88 of the Y-site 36 after the piercing member 98a of the blunt cannula 86 has been forced through the preformed opening.

The cannula shown in FIGS. 14–18 may be used with the Y-site alone, or may be incorporated into a bayonet locking cannula to achieve a locked blunt cannula/Y-site connection as will be described later.

Figure 14:
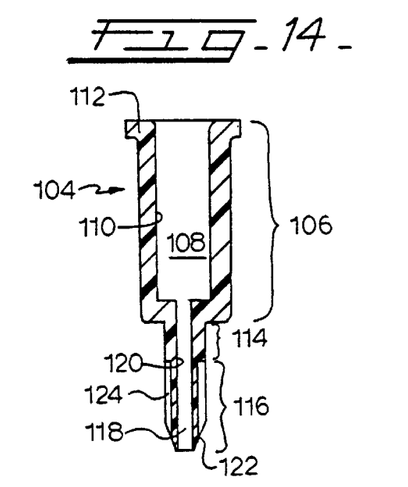
FIG. 14 is a sectional view of a first embodiment of a blunt cannula.
Figure 15:
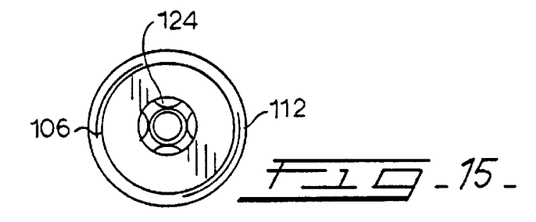
FIG. 15 is a top view of the blunt cannula of FIG. 14.

FIGS. 14 and 15 illustrate a tapered cannula structure 104 which is a first embodiment that can be used with the Y-site 36 or may incorporated into the bayonet locking cannula 82. The cannula includes a proximal end 106 with an interior region 108. The interior region 108 is in part bounded by an internal peripheral wall 110 which is formed with a standard luer taper. The tapered cannula 104 can be formed with a luer-type coupling flange 112 at the proximal end so as to be releasably connected to another medical device, such as a syringe.

Extending from the proximal end 106 is a cylindrical tube having a cylindrical mid-region 114 and a distal end member 116. The distal end member 116 has a generally elongated, cylindrical shape with a exterior side wall 120. A centrally located, cylindrical, internal fluid flow path 118 extends through distal end member 116 and mid-region 114 and fluid flow communication with the interior region 108. The distal end of end member 116 has a tapered exterior surface 122. The tapered exterior surface 122 minimizes insertion force of the cannula 104 is being forced through a slit of the septum, such as the slit 66 of septum 52. The angle of taper of the surface 122 is preferably in the range between 1 to 15 degrees.

The distal end member 116 is also provided with a plurality of elongated grooves 124. The grooves 124 in the exterior wall of the distal end member 116 decrease the surface area contact at the cannula/septum interface during insertion of the cannula and to the Y-site 36. This reduce exterior contact surface area decreases the frictional component of the insertion force.

Figure 16:
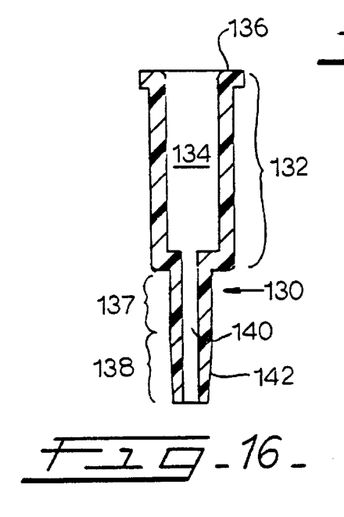
FIG. 16 is a second embodiment of a blunt cannula.
Figure 17:
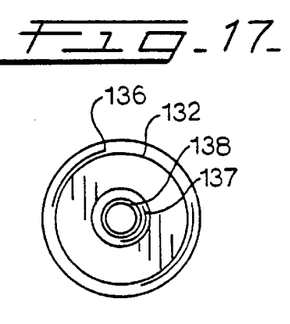
FIG. 17 is a top view of-the blunt cannula of FIG. 16.

In one embodiment, the tapered blunt cannula 104 may have an overall insertion length, corresponding to the axial length of mid-region 114 and end member 116, on the order of 0.375 inches. An alternate cannula structure, identified generally as numeral 130, is shown in FIGS. 16 and 17. The cannula 130 includes a proximal end 132 defining an interior region 134 and having a luer-type flange 136 for connection to a suitable mating engaging surface.

A generally cylindrical mid-region 137 extends between the proximal end 132 and a distal end region 138. The embodiment of the cannula 130 minimizes kick back or recoil due to the provision of substantially cylindrical mid-region 137. This design also increases tug resistance to reduce inadvertent withdrawal.

A generally cylindrical internal flow channel 140 extends through the end region 138 and mid-region 137 in communication with the interior region 134 of the proximal end region 132. The end region 138 is provided with a tapered surface 142. The design permits of a very small taper to minimize the insertion force. Further the design permits the cannula 130 to be constructed with a small tip diameter, small tapered angle and small cannula diameter so as to reduce the peak insertion force.

Figure 18:
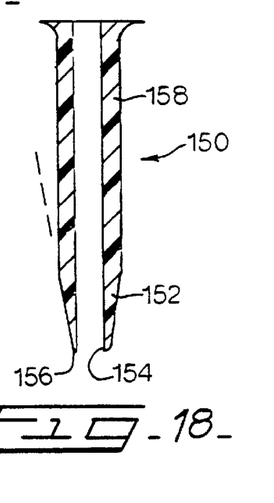
FIG. 18 is a third embodiment of a blunt cannula.

Still another embodiment is illustrated in FIG. 18 which shows a blunt tapered cannula insertion member 150 for insertion into the pre-slit injection Y-site. The cannula 150 has a distal end region 152 with a tapered exterior surface in which the preferred embodiment is an approximately 8°. The defined apperture 154 for fluid flow is disposed at the end region 156 of the distal end region 152. The end 156 includes a radiused tip defined by a radius of approximately 0.01 inch. The radiused tip reduces insertion force, assist in locating the slit in the injection site and in addition has the practical advantage of facilitating complete filling of the cannula mold cavity.

The tapered surface of the distal end region 152 has an axial length of approximately 0.10 inches in the preferred embodiment. Adjacent to the tapered distal end region is a generally cylindrical region 158 for entering into the injection site behind the distal end region 152, thereby reducing kick back during insertion. The generally cylindrical region 158 has a small draft angle such as about one-half degree.

The force required to insert any of the above-discussed embodiments of a blunt tapered cannula into the septum of the injection site depends upon a number of factors: friction at the cannula/septum interface, cannula diameter, cannula tapered angle, and degree of septum compression. The cannula/septum interface friction is, in turn, dependent upon lubrication, if any, material properties and surface finish. It will be understood that the friction at the cannula/septum interface can be reduced by providing a smoother surface finish on the cannula (e.g., by sandblasting the cannula exterior surface) or by molding the cannula so as to produce a matte finish. Conventional lubricants can also be used to further reduce friction and thereby lower the insertion force required.

The deformation of the septum 52 also facilitates insertion of the piercing member 98 through the slit or opening 66. Subsequent to the piercing member 98 slidably engaging the Y-type injection site or Y-site 36, the interior region of the tubing 192 to which the bayonet locking cannula 82 is connected is in fluid flow communication with the flow path 68 of the Y-site 36 via the flow path of the blunt piercing member 98.

In this engagement condition, the septum 52 seals completely around the piercing member 84. Hence, exterior gases, liquids or airborne matter will be excluded from the flow path 68.

Subsequent to infusing fluid from the bayonet locking cannula 82 into the fluid flow pathway 68, hence to the patient, the bayonet locking cannula 82 with lockingly engaged shielded cannula 86 can be slidably withdrawn from the injection site 34. Subsequent to this withdrawal, the septum 52 reseals the opening or slit 53 therein.

The opening 53 will repeatedly reseal, when the piercing member 98 is removed, provided that the pressure (in the septum 52) created by interaction of the septum material properties and compression supplied by the housing exceeds the pressure challenge of the fluid contained within. Blunt cannula do not haphazardly core, lacerate, or otherwise damage the sealing interface of slit 53 as conventional needles do, thereby allowing repeatable resealability. However, septum material properties, thickness, and compression allow resealability for a finite number of conventional needle insertions. The Y-site 36 then returns to its pre-infusion, sealed condition.

As an alternate to forming the slit 66 completely through the septum 52, as illustrated in FIG. 4 a slit 66a can be formed only partly through the septum 52. Such a structure has the further advantage that until used for the first time the septum 52 is completely sealed.

The septum 52 can be formed in two parts. One part can have a slit, such as the slit 66 extending entirely therethrough. A second part can be formed without a slit. These two parts can be located adjacent one another in first end 72 of the injection site.

The slit may be longer on the top of the septum than the bottom. This feature aids blunt cannula alignment with the slit upon insertion, and aids resealability by minimizing the critical slit sealing interface area.

In accordance with the present invention, the slit 53 could have a length with a range on the order of 0.03 to 0.150 inches. Preferably, a slit length in the order of 0.07 inches will be used in combination with a blunt cannula having a diameter on the order of 0.1 inches.

When initially used, the blunt cannula piercing member 98 will be forced through the slit 66a. The lower peripheral surface of the septum 52 will then be punctured, providing access for the blunt cannula piercing member 98 into the fluid flow pathway 68.

FIGS. 20–24 disclose a method of making a pre-slit injection site in accordance with the present invention. In a first step, a housing 200 is provided. The housing 200 has an interior tapered surface 202 at a first end 200a thereof. The interior peripheral surface terminates in an annular channel 204. A cylindrical septum 206 can be provided adjacent the end 200a.

Figures 20, 21:
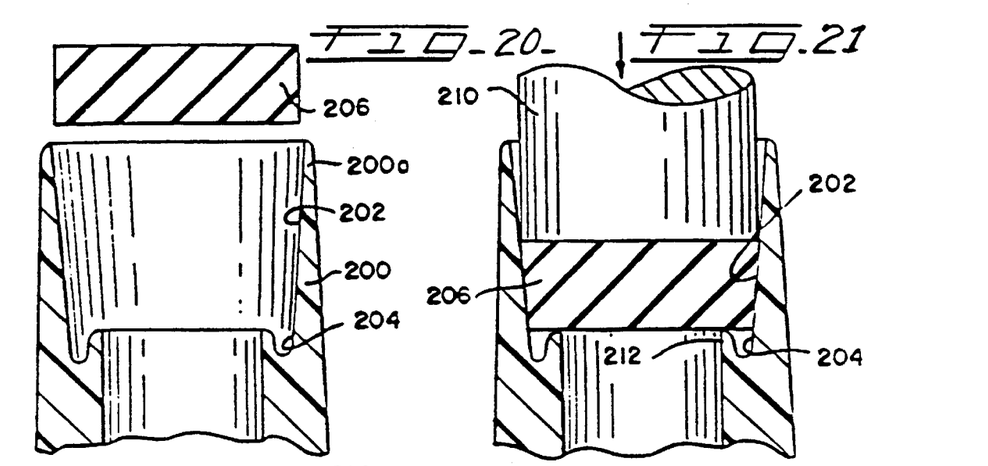
FIG. 20 is a step in the method of making a pre-slit injection site in accordance with the present invention.
FIG. 21 is another step in the method of making a pre-slit injection site in accordance with the present invention.

In a second step, the septum 206 can be forced into the end 200c of the housing 200o and slightly deformed by the tapered peripheral surface 202 using an axially moving die 210. When positioned by the die 210, the septum 206 is located adjacent an internal annular ring 212 which bounds the annular channel 204.

Figure 22:
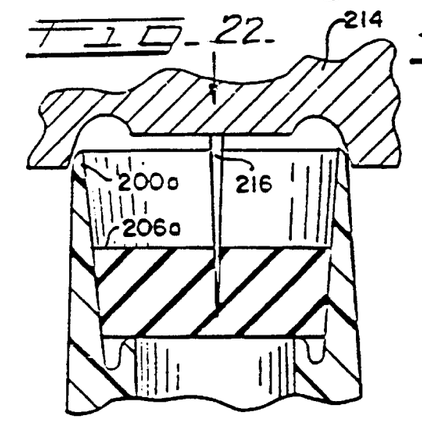
FIG. 22 is an initial phase of a final step in making a pre-slit injection site in accordance with the present invention.
Figure 23:
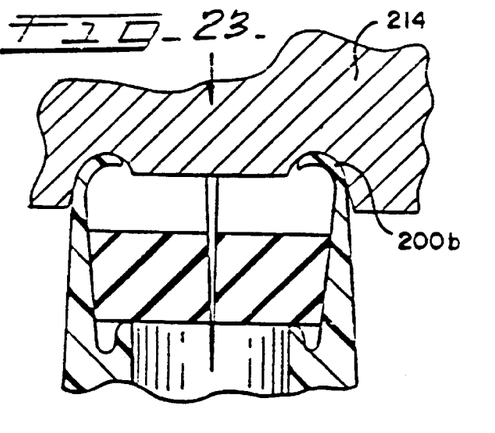
FIG. 23 is an intermediate phase of the final step in a method of making a pre-slit injection site in accordance with the present invention.

In a third step, a second die 214 can be utilized to swag the end 200a into spiral-shaped, spring-like members 200b which apply axially directed forces against an exterior peripheral surface 206a of the septum 206. The axially directed forces form the flat surface 206a into a domed exterior peripheral surface 206b as illustrated in FIG. 23.

Figure 24:
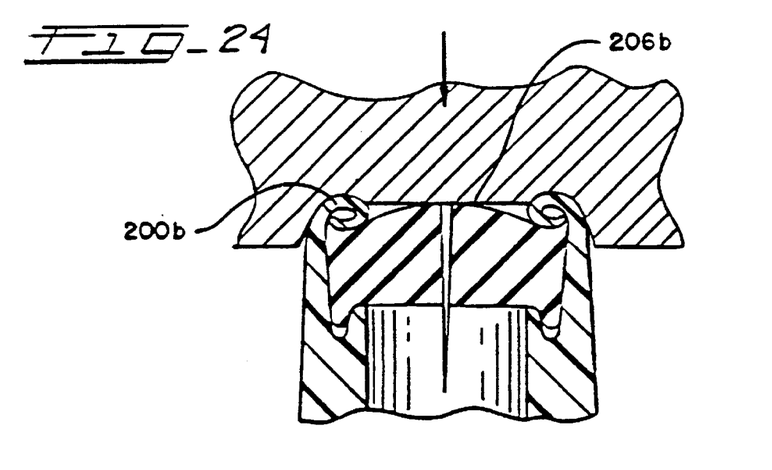
FIG. 24 is a final phase of the final step in a method of making a pre-slit injection site in accordance with the present invention.

Simultaneously, with swaging the end members 200a so as to lock the septum 206 into the housing 200 and to form the domed exterior peripheral surface 206b, a knife 216 can be utilized to form a slit in the septum 206. Alternatively, the slit may be cut by a separate die in a separate step. If the septum 206 is formed as an extrusion, the slit can be created during the extrusion process. If the septum 206 is formed by stamping from a rubber sheet, the slit can be cut during the stamping process. If the septum 206 is formed by compression molding, the slit can be cut during the trimming process.

In order to extrude the slit into rod, a flat pin extrusion bushing can be used. A trailing ribbon may be attached to the bushing. The ribbon would prevent curing material across the slit. The ribbon or wire could be placed in the rod core and later stripped out leaving a slit. An inert substance, such as silicone oil, could be coextruded in the center of the rod to prevent curing across the slit and provide lubrication and a visible target for cannula insertion.

Figure 25:
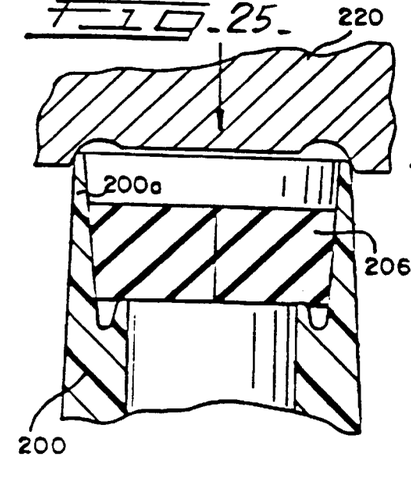
FIG. 25 illustrates an initial phase in an alternate step of making a pre-slit injection site in accordance with the present invention.
Figure 26:
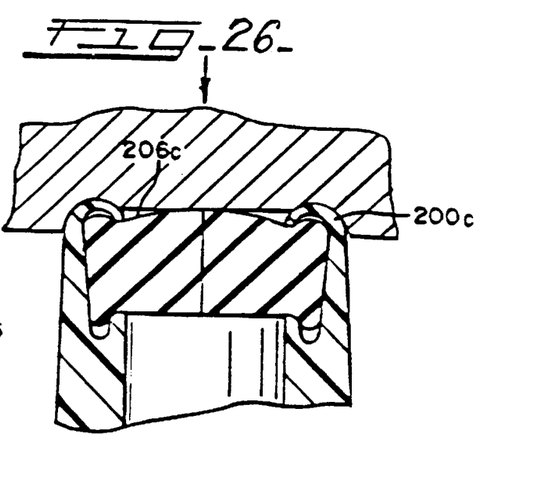
FIG. 26 illustrates a final phase of the alternate step in a method of making an injection site in accordance with the present invention.
Figure 27:
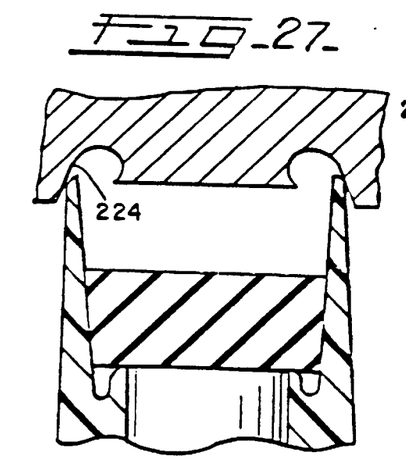
FIG. 27 illustrates yet another alternate step in a method of making a pre-slit injection site in accordance with the present invention.

FIGS. 25 and 26 illustrate alternate swaging steps wherein a die 220 moving axially toward the housing 200 sages the end region 200a so as to form an annular U-shaped region 200c and the exterior domed peripheral surface 206c.

The dies 214 or 220 can be formed with various alternate shaped swaging surfaces 224, as illustrated in FIG. 26, depending on the precise shape of the end swage which is desired. It will be understood that all such variations in the swaging operation are within the spirit and scope of the present invention.

Figure 28:
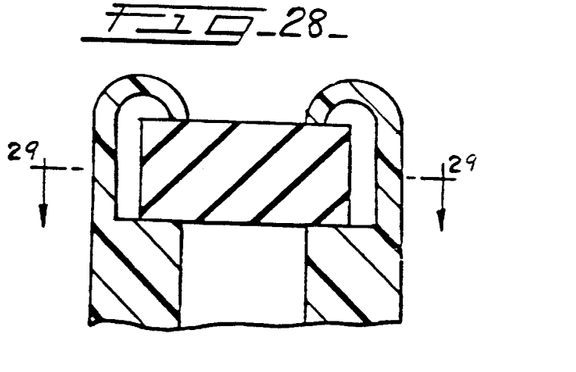
FIG. 28 is an enlarged, fragmentary cross-sectional view of another embodiment of an injection site in accordance with the present invention.
Figure 29:
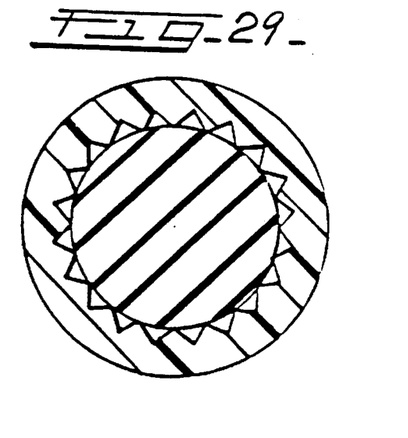
FIG. 29 is a cross-section view taken generally along the plane 29—29 in FIG. 28.

The injection site configuration need not be limited to the configurations depicted in the figures. Rather, several configurations could be constructed without departing from the scope of this invention. Any such configuration would provide a flexible pre-slit sealing member captured in a housing which provides compression to create a seal against pressure and a void region accessible to the sealing member material only when displaced by a blunt cannula piercing member. One such possible configuration is depicted in FIGS. 28 and 29.

In the embodiments of the cannulae described herein, the mid-region and the tapered distal end region may be alternatively characterized as together forming at least one tube defining a fluid flow path therein with the tube having a distal end region for penetrating the injection site.

In preferred contemplated embodiments, the exterior surface of the distal end region may have a taper angle as small as between one and fifteen degrees.

Figures 6, 7:
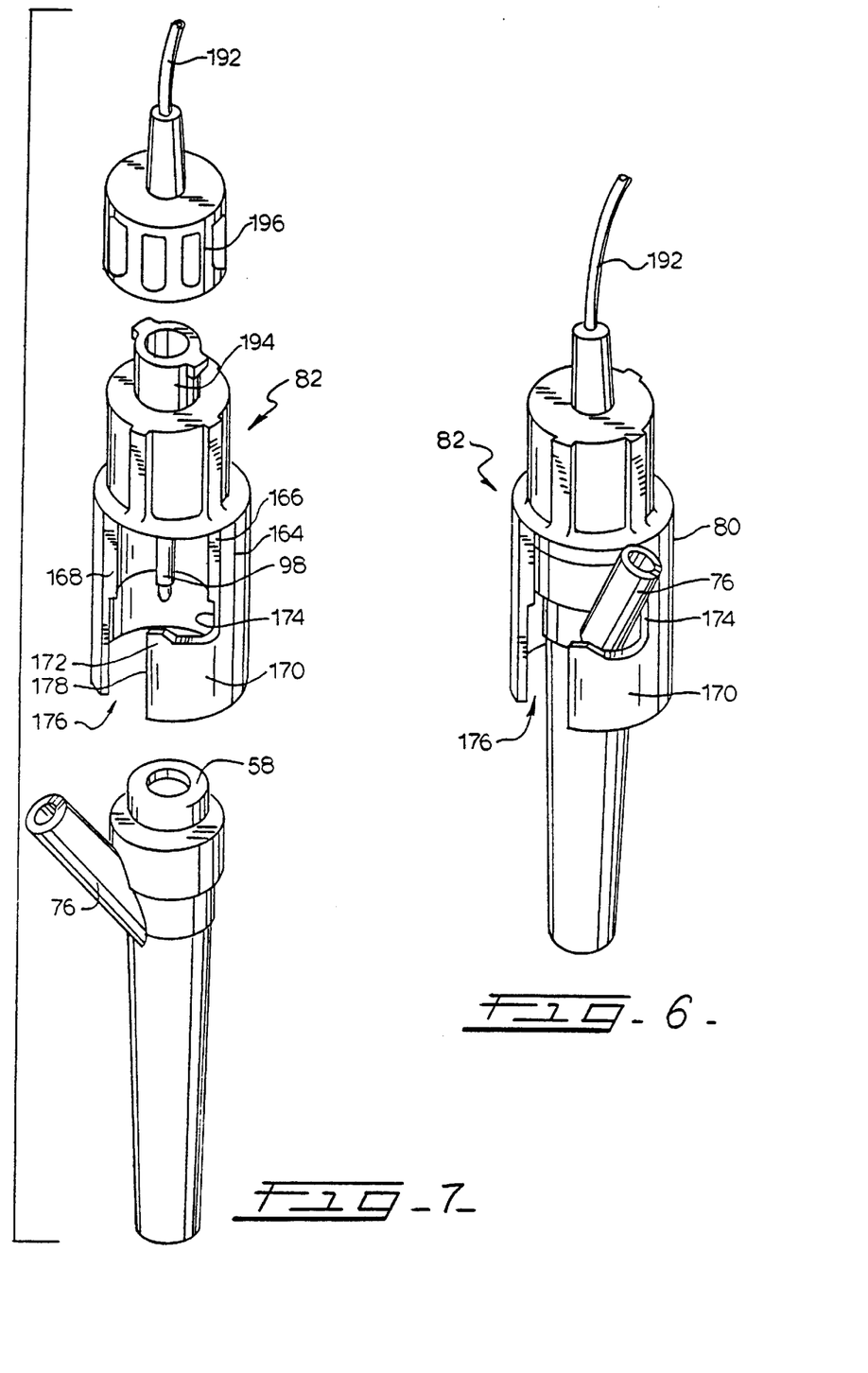
FIG. 6 is a perspective view of a pre-slit Y-site and bayonet lock cannula bounded to tubing.
FIG. 7 is an exploded perspective view of a pre-slit Y-site and bayonet lock cannula with a luer lock connection to tubing.
Figure 13:
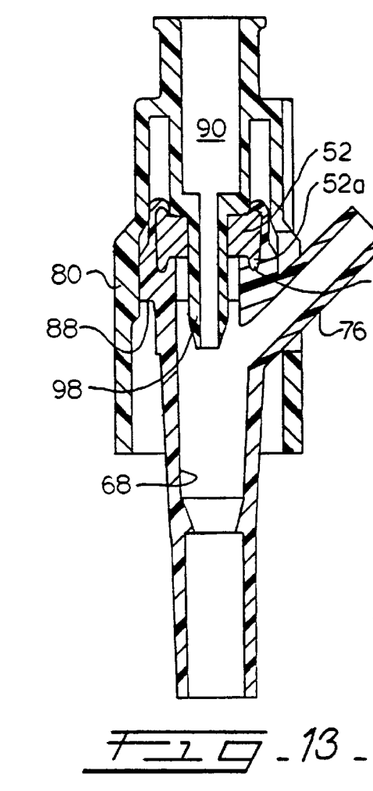
FIG. 13 is a side sectional view of the pre-slit Y-site with bayonet lock cannula in the locked position.

As shown in FIG. 6, the bayonet locking blunt cannula 82 includes a cylindrical hollow protective shield 80 which surrounds a centrally located hollow, elongated cylindrical blunt piercing member 98. The cylindrical blunt piercing member 98 has a total length on the order of 3 times the thickness of the septum 52 in order to ensure complete penetration. The cylindrical blunt piercing member 98 has a diameter on the order of ⅓ the diameter of the septum 52. The blunt piercing member 98 can slidably engage the septum 52 and extend through the preformed opening 66. As illustrated in FIG. 13, when the piercing member 98 slidably engages and pierces the septum 52, the region 52a deforms by expanding into and filling, at least in part, the annular channel 62.

The bayonet locking cannula 82 shown in FIG. 6 includes a blunt cannula similar to that shown for example in FIG. 16 in addition to a protective shield 80. Protective shield 80 includes an arcuate wall 164 that extends approximately 180–200° from side 166 to flat side 168. The arcuate wall 164 provides substantial shielding to the blunt piercing member 98 to maintaining the piercing member 98 in an aseptic condition by preventing touch contamination prior to its being inserted into the pre-slit septum 52.

Protective shield 80 also includes a bayonet arm 170 which ends in a bayonet barb 172 to create an opening or bayonet lock 174. As the bayonet locking cannula 82 is pushed onto the Y-site 36, Y-site arm 76 passes through the gap 176 between the end 178 of the bayonet arm and side 168. When the bayonet cannula 82 is pushed as far as possible onto the Y-site 36, then the Y-site can be rotated with respect to the bayonet lock, causing the side arm 76 to pass over the bayonet barb 172 and into the bayonet lock 174.

Because the Y-site 36 is part of an administration set 42 which provides fluid to the patient for a relatively long period of time, it is important that leaks be reduced. Leaks may occur at the Y-site if the blunt piercing member is misaligned with the Y-site septum. 52 by more than acceptable tolerance. Such leaks are quite undesirable because of the medical implications.

The bayonet lock cannula 82 and the Y-site 36 have three zones of docking to provide for correct alignment. These zones of interference are indicated on FIG. 19.

Figure 19:
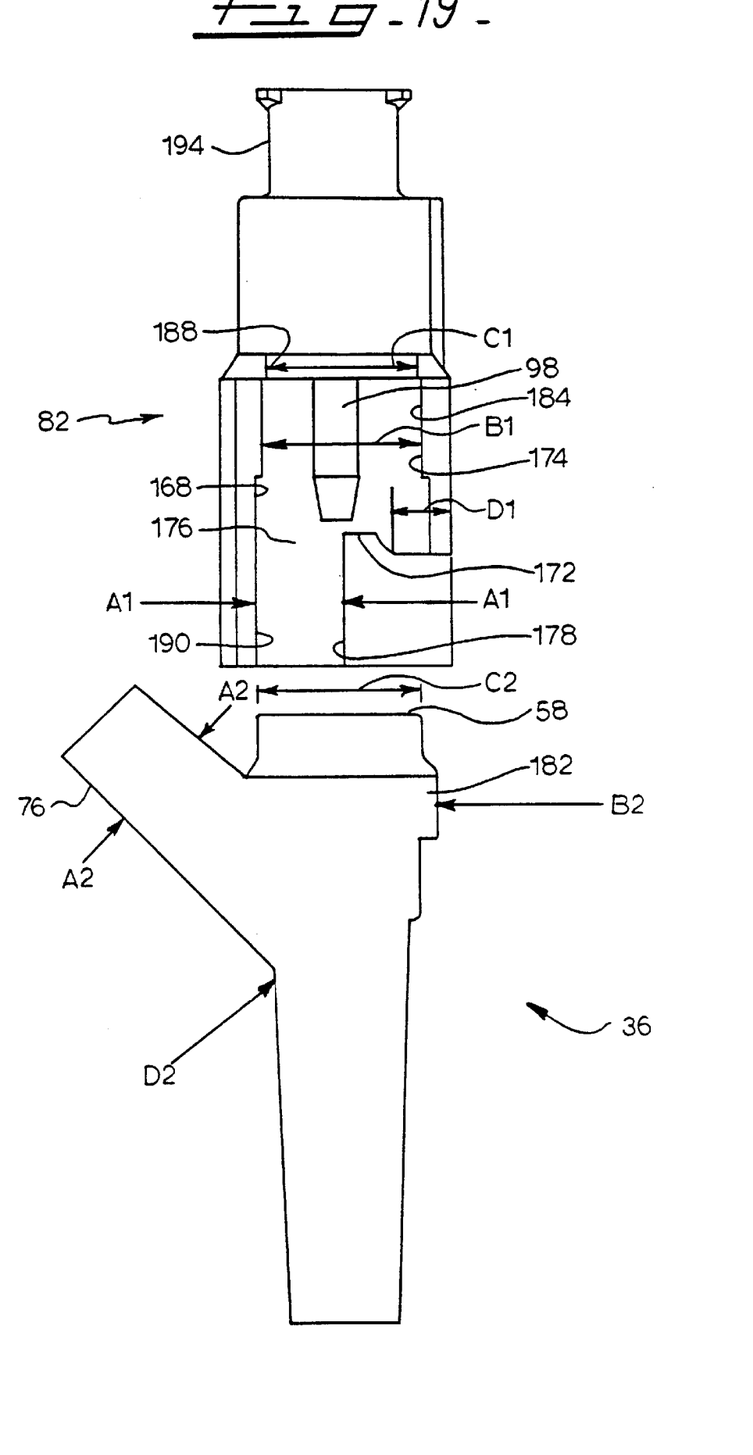
FIG. 19 is a schematic exploded side view of the pre-slit Y-site and bayonet lock cannula with zones of interference marked.

The first zone of interference is indicated by A1 and A2 on FIG. 19. As the bayonet lock cannula 82 is moved onto the Y-site 36, Y-site arm 76 moves through gap 176 between the end 178 of bayonet arm and flat side 168. Gap 176 is smaller than the diameter of diameter of Y-site arm 76. For example, the gap 176 may be 0.200" while the diameter Y-site arm is 0.220" to create a positive interference of 0.010" per side.

The second zone of interference is indicated by B1 and B2 on FIG. 19. After the piercing member 98 begins to penetrate the opening 66 of septum 52, the housing shoulder 182 of the Y-site 36 and the first interior mid-region 184 of protective shield 80 engage to create additional interference and directional guidance between the two components. The housing shoulder 182 and the first interior mid-region 184 should have a positive interference of, for example, 0.001" per side or 0.0025" per side. There should be a maximum positive interference between these two areas of 0.004".

The third zone of interference between the Y-site 36 and the bayonet lock cannula 82 is zone C, indicated by C1 and C2 on FIG. 19. As the bayonet lock cannula 82 continues to move onto Y-site 36, swage the member 58 holding the septum 52 in compression on Y-site 36 engages the second interior mid-region of protective shield 80. The second interior mid-region 188 has a diameter that is smaller than the first interior mid-region 184 which has a diameter that is smaller than the diameter of the outer interior region 190. As the swage member 58 contacts the second interior mid-region 188, the injection site is now docked and ready for engagement within the bayonet lock 174.

The Y-site 36 is engaged by rotating the Y-site arm 76 past the bayonet barb 172 into the bayonet lock 174 thereby engaging a mechanical lock as indicated by D1 and D2. The dimensions of the Y-site 36 and bayonet lock cannula 82 are such that when the septum 52 is higher than the swage member 58 the septum 52 must be compressed a slight amount against the cannula 82 to rotate Y-site arm 76 past the bayonet barb 172. When the Y-site arm 76 is properly positioned within bayonet lock 174, the septum 52 is still compressed a slight amount. The compression of the septum 52 and the drag from the cannula 82 against the septum 52 require a predetermined torque to engage the Y-site 36 and to disengage the Y-site arm 76 from the bayonet lock 174.

The dimensions of the bayonet lock cannula 82 and Y-site 36 used in creating the zones of interference must be carefully calculated so that the torque is not so large that in engaging or disengaging the Y-site 36 from the bayonet lock 174, components adjacent to the Y-site 36 and bayonet lock cannula 174 are disconnected. FIG. 6 shows a bayonet lock cannula 82 bonded to tubing 192 while FIG. 7 shows a bayonet lock cannula 82 having a luer fitting 194 which mates with a luer cap 196 which is bonded to tubing 192. American National Standards Institute standards require that a locking luer fitting must not disconnect until 3 inch ounces of force is exerted on it. If the connection or disconnection of the Y-site arm 76 from the bayonet lock 174 requires more force than 3 inch ounces, the luer cap 196 may be accidentally disconnected from the luer fitting 194.

Figure 8:
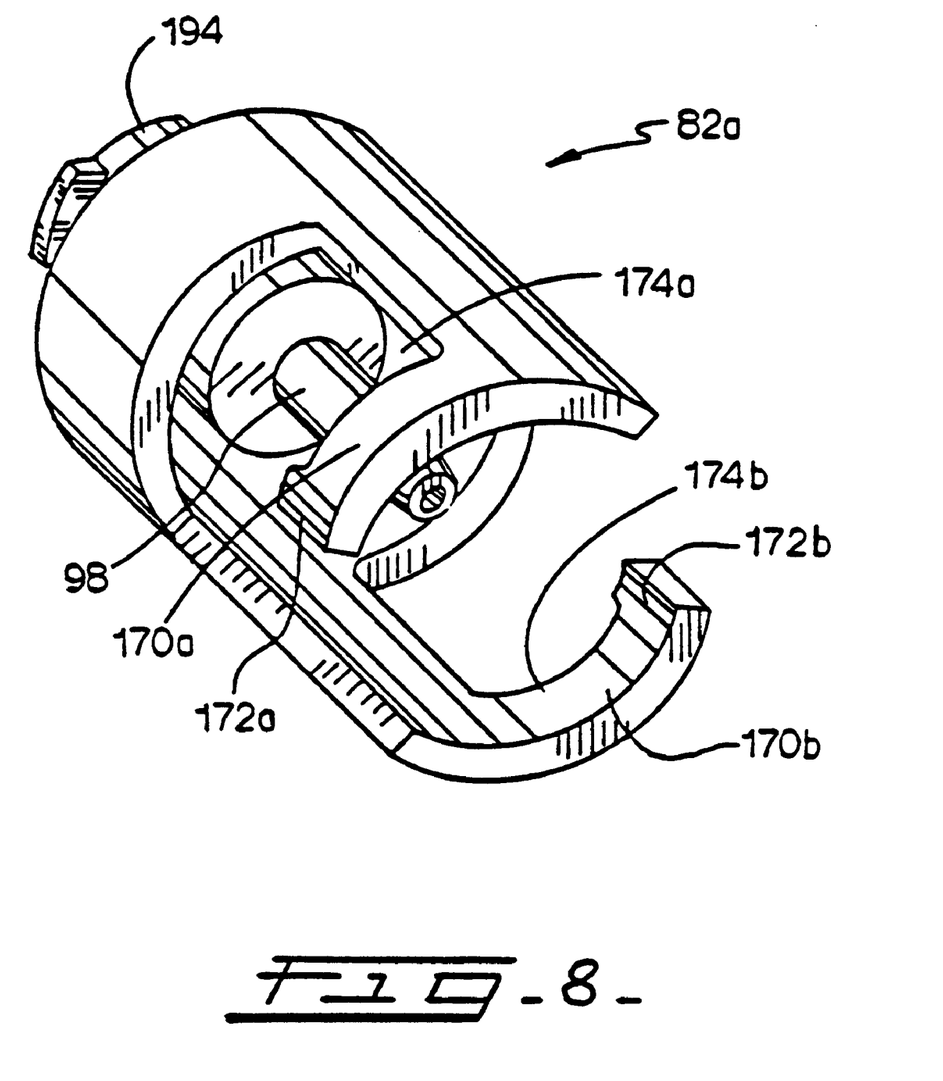
FIG. 8 is a perspective view of a bayonet lock cannula having two bayonet locks.
Figure 9:
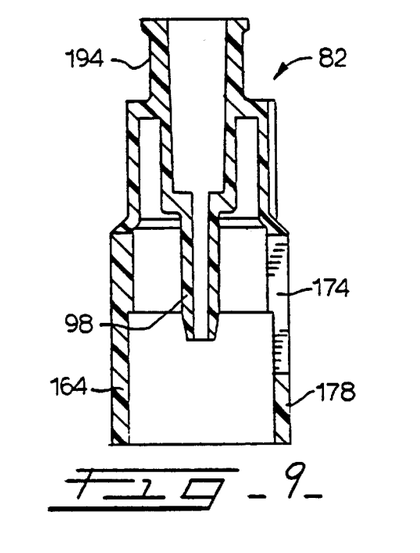
FIG. 9 is a side view in section of the bayonet lock cannula.
Figure 10:
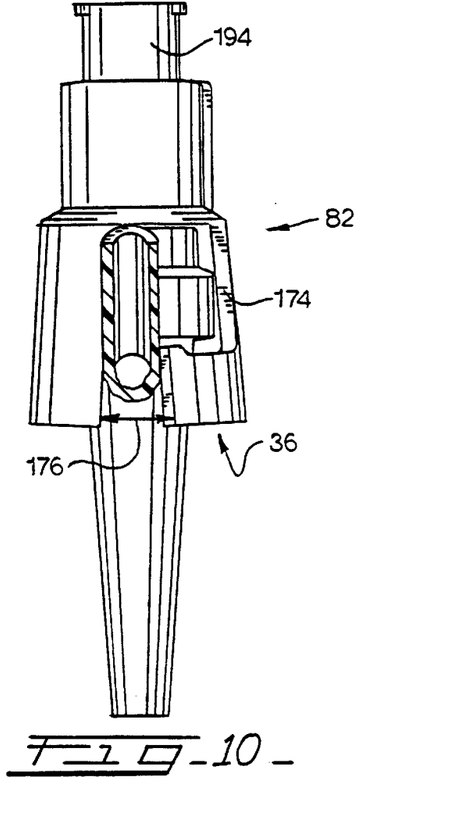
FIG. 10 is a perspective view with a partial sectional of the pre-slit Y-site with bayonet lock cannula.
Figure 11:
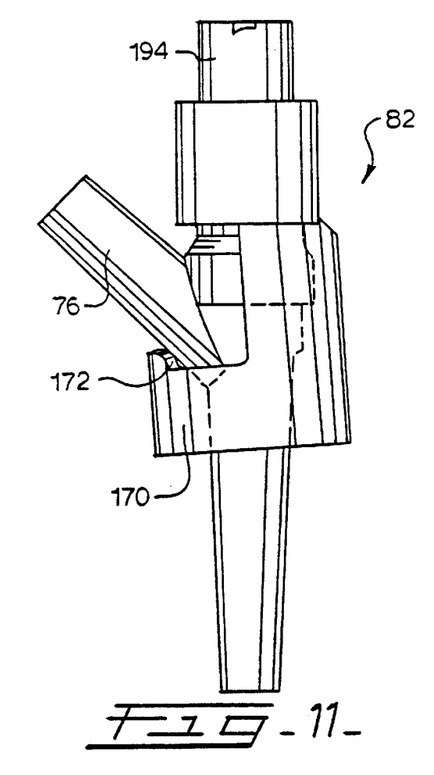
FIG. 11 is a side view of the pre-slit Y-site with bayonet lock cannula.
Figure 12:
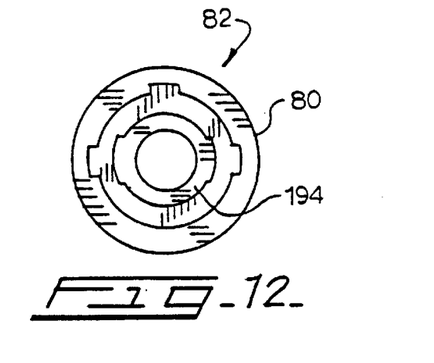
FIG. 12 is a top view of the bayonet lock cannula with a luer lock connection.

An alternative embodiment of the bayonet lock cannula 82 is shown in FIG. 8 and generally identified as 82*a*. Bayonet lock cannula 82*a* includes two bayonet arms 170*a*, two bayonet barbs 172*a*, 172*b*, and two bayonet locks 174*a*, 174*b* which mate with the two arms of a T-type connector with injection site or T-site (not shown).

From the foregoing, it will be observed that numerous variations and modifications may be effected without departing from the spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

We claim:

1. A system for connecting a secondary flow of fluid to a primary flow of fluid along a flow path to a patient, the system comprising:

a Y-site having a first end, a second end and an arm, a portion of the flow path defined by an inlet tubing connected to the arm, the Y-site, and an outlet tube connected to the second end, the first end being generally tubular, the Y-site also including a septum compressingly disposed within the first end, the septum having a resealable opening therein such that a blunt cannula can be sealing inserted through the opening and placed in fluid flow communication with the flow path; and a connector having, the blunt cannula forming a passageway for the second fluid flow, and an annular protective shield spaced radially outward from and at least partially surrounding said cannula, the shield having an internal surface dimensioned to slide about the first end of the Y-site, the protective shield defining a gap extending from an end of the shield and also defining a generally circumferentially extending opening connected to the gap, the opening being at least partially defined by an arcuate arm forming a portion of said shield, the gap being formed so that said Y-site arm may pass along said gap as said shield is slid about the first end of the Y-site until said Y-site arm is radially aligned with said opening, said opening being formed so that said Y-site arm may then pass within said opening and along said arcuate arm when said connector is rotated relative to said Y-site to releasably engage said connector to said Y-site.

2. The system of claim 1 wherein the arcuate arm includes a barb configured to releasably engage said Y-site arm when said arm is passed over said barb as said connector is rotated relative to said Y-site.

3. The system of claim 1 wherein the gap is formed so that the width of said gap is less than the diameter of said arm so that an interference between the Y-site arm and shield on both sides of the gap is created when the Y-site arm passes along the gap.

4. A method of connecting a secondary fluid flow through a connector to a primary fluid flow along a flow path through a Y-site, the Y-site having a first end, a second end and an arm, the flow path defined by an inlet tubing connected the arm, the Y-site, and an outlet tube connected to the second end, the first end being generally tubular, the Y-site also including a pierceable preslit septum compressingly disposed within the first end, the connector having a blunt cannula forming a passageway for the second fluid flow, an annular protective shield spaced radially outward from and at least partially surrounding said cannula, the shield having an internal surface dimensioned to slide about the first end of the Y-site, the protective shield defining a gap extending from an end of the shield and a generally circumferentially extending opening connected to said gap, the opening being at least partially defined by an arcuate arm forming a portion of said shield, the method comprising the steps of:

advancing the shield slidingly about the first end of the Y-site while penetrating the pre-slit septum with the cannula to connect the passageway to the flow path, said advancing including passing the arm into and along the gap until the arm is radially aligned with the opening;

rotating the connector relative to the Y-site, said rotating including passing the Y-site arm within the opening and along the arcuate arm to releasably engage the connector to the Y-site by interconnecting the arm of the Y-site to the shield.

5. The method of claim 4 wherein the arcuate arm includes a barb configured to releasably engage said Y-site arm and said rotating step includes passing the Y-site arm over said barb as said connector is rotated relative to said Y-site.

* * * * *